United States Patent [19]

Le Dain et al.

[11] 4,421,653
[45] Dec. 20, 1983

[54] PROCESS FOR THE DEPROTEINIZATION OF BIOLOGICAL FLUIDS

[75] Inventors: Michel Le Dain, Neuwiller, France; Werner Ritschard, Kaiseraugst, Switzerland

[73] Assignee: Hoffmann-La Roche Inc., Nutley, N.J.

[21] Appl. No.: 408,311

[22] Filed: Aug. 16, 1982

Related U.S. Application Data

[62] Division of Ser. No. 231,400, Feb. 4, 1981, abandoned.

[30] Foreign Application Priority Data

Feb. 8, 1980 [CH] Switzerland .......................... 1037/80

[51] Int. Cl.³ ............................................. B01D 15/00
[52] U.S. Cl. ..................................... 210/692; 210/927
[58] Field of Search ............... 210/692, 782, 787, 806, 210/927; 260/112 R; 436/67, 86, 87, 88, 174, 178; 525/382

[56] References Cited

U.S. PATENT DOCUMENTS

| 3,415,745 | 12/1968 | Isaacson | 260/78.5 |
| 3,455,827 | 7/1969 | Mehmedbasich et al. | 252/32.7 |
| 3,506,625 | 4/1970 | Patinkin et al. | 260/78.5 |
| 3,554,985 | 1/1971 | Fields et al. | 260/78.5 |
| 3,655,509 | 4/1972 | Fields et al. | 424/79 |
| 3,810,276 | 5/1974 | Morduchowitz | 117/132 B |
| 4,157,431 | 6/1979 | Fields et al. | 526/15 |

Primary Examiner—Ivars C. Cintins
Attorney, Agent, or Firm—Jon S. Saxe; Bernard S. Leon; George M. Gould

[57] ABSTRACT

There is described a deproteinizing agent comprising a water insoluble crosslinked polycarbonic acid formed by crosslinking a polymeric compound with a diamine. This deproteinizing agent is useful for deproteinizing biological fluids.

8 Claims, No Drawings

PROCESS FOR THE DEPROTEINIZATION OF BIOLOGICAL FLUIDS

This is a division of application Ser. No. 331,400 filed Feb. 4, 1981, now abandoned.

BACKGROUND OF INVENTION

Numerous methods for deproteinization of biological fluids are described in the article "Review of Methods for Removing or Solubilizing Proteins in Biological Fluids" by Robert G. Martinek in J. Am. Med. Technol. 32, 345–381 (1970). It is common to all of these methods that they are relatively expensive with regard to the time which is needed as well as with regard to the apparatuses which are required.

There accordingly exists a real need for a more simple and reliable method for the deproteinization of biological fluids.

SUMMARY OF INVENTION

The present invention relates to the deproteinization of biological fluids by removing the water insoluble phase after adding to the fluid a water insoluble crosslinked polycarbonic acid obtained by crosslinking a polymer of the formula

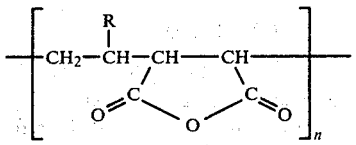

wherein R is hydrogen or lower alkoxy and n is a whole number of 100–10,000,
with a diamine and hydrolysing unreacted anhydride groups.

The process provided by the present invention is especially useful for the purification of biological fluids containing protein, especially glycoproteins. The process can, however, also be used for the purification of other polysaccharide substances which remain in the supernatant after the deproteinization.

Furthermore, the present process can also be used in clinical chemistry when the deproteinization presents disadvantages, for example when plasma proteins or serum proteins disturb the detection reaction of the particular method and the substance to be determined must be detected in the supernatant. Whole blood samples can also be deproteinized in a similar manner.

DETAILED DESCRIPTION OF THE INVENTION

The present invention relates to a process for the deproteinization of biological fluids by using a water insoluble crosslinked polycarbonic acid as deproteinizing agent which is formed by crosslinking a polymer compound of formula I with a diamine and hydrolysing unreacted anhydride groups. Particularly the present invention relates to a process for deproteinizing a biological fluid, comprising:
(a) adding to the fluid a water insoluble crosslinked polycarbonic acid formed by crosslinking a polymer of the formula

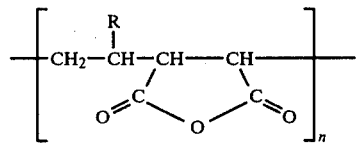

wherein R represents hydrogen or lower alkoxy and n represents a whole number of 100–10,000; with a diamine and hydrolysing unreacted anhydride groups and
(b) removing the resulting water-insoluble phase from the fluid.

Furthermore the present invention encompasses a composition of matter formed by crosslinking a polymer of formula I with a diamine and hydrolysing unreacted anhydride groups.

The symbols of the atoms shown in the brackets of formula I represent the repeating unit of the polymer, and n represents the number of such units in the polymer before crosslinking the polymer with a diamine. The units as represented by n may vary from 100 to 10,000. It is preferred that the symbol R in formula I is hydrogen. Such a polymer, wherein n is from 120 to about 250 can be obtained from Monsanto Chemical Co., St. Louis, Missouri, U.S.A. under the name ethylene-maleic acid anhydride copolymer (EMA). Also preferred is a polymer of formula I wherein R is methoxy. Such a polymer, wherein n is from about 3000 to about 7500 can be obtained under the name Gantrez AN from GAF Corp., Chemical Division, New York 10020, U.S.A.; this product is a poly(methyl vinyl ether/maleic anhydride.

The term "lower alkoxy" comprehends groups having from 1 to 7 carbon atoms, such as methoxy, ethoxy and the like.

In the deproteinization of biological fluids by the present process of the invention, it is possible to use any biological fluid containing protein desired to be removed and includes such fluids as whole blood, plasma, sera, lymph, bile, urine, liquor, spinal fluid, sputum, sweat and the like as well as stool excretions. It is possible also to use fluid preparations of human or other animal tissue such as skeletal muscle, heart, kidney, lungs, brain, skin tumour extracts and the like, including cell culture extracts or milk or microbiological culture fluids or plant extracts. The preferred biological fluid is human sera and tumour extract, especially human liver metastases.

The crosslinking of the polymer of formula I can be carried out with any diamine in any conventional manner well-known in the art. Among the art recognized diamines, ethylenediamine and hexamethylenediamine are especially suitable and preferred. Typically the polymer of formula I is crosslinked with a diamine in water or in an organic solvent, such as acetone. The reaction may be carried out at atmospheric pressure at room temperature or elevated temperature. The diamine converts by the cross-linking reaction the anhydride groups of the polymer of formula I into carboxy and amide groups. Unreacted anhydride groups are converted into carboxy groups by hydrolysis in an aqueous medium. After the reaction is completed an aqueous phase may be added to the mixture, the organic phase removed conventionally as by evaporation under vacuum, and the residue dried at room temperature to provide the deproteinizing agent. The resulting deproteinizing agent can be used in the process of the invention in the form of an emulsion, a suspension, a solution or as a dry powder. It is preferred that the deproteinizing agent be used in the form of a 1–10% aqueous suspension or as a pulverous dry substance or fixed to an inert carrier such as, for example, glass or metal.

The ratio of the deproteinizing agent to the biological fluid can vary according to the degree of deproteinization desired. The optimum ratio is, however, preferably determined in each case having regard to the concentration of proteins, the nature and the concentration of the substance to be purified, the temperature, the pH-value and the ion concentration. The temperature and the pH-value are, in principle, not critical. However, the temperature generally lies between 0° and 100° C., preferably between 4° C. and 25° C., and the pH-value is adjusted to a value between 3 and 10 using a suitable buffer such as, for example, a phosphate, acetate or tris buffer. In each case, however, the temperature and the pH-value as well as the ion strength must be determined individually. This, however, is well known to a person skilled in the art.

The degree of the deproteinization depends on the density of the reactive groups in the deproteinization agent. The density of the reactive groups is not critical for the operability of the invention provided that an adequate quantity thereof is present in order to guarantee the bonding of a sufficient quantity.

Typically the deproteinization agent is added to the biological fluid and after a fixed time (generally 5 to 15 minutes) of intensive contact (e.g. by stirring), the water-insoluble phase is removed. This removal can be carried out by any conventional method customary for phase separation (e.g. centrifugation, filtration or sedimentation). The removal of the water-insoluble phase provides, thereby, a deproteinized residue.

A variant of the present deproteinization process consists in extracting a substance, which is precipitated by the deproteinization agent or is precipitated therewith, from the precipitate by a suitable treatment such as, for example, by the use of special buffer solutions or other extraction agents. This variant can be used preparatively or analytically.

The deproteinized residue (the deproteinized fluid remaining behind after deproteinization) can be further processed in any manner. For preparative purposes (e.g. for the purification of peptides, glycoproteins, steroids, lipoids, nucleic acids, enzymes, hormones, vitamins, polysaccharides or alkaloids) further purification steps can, for example, be carried out. In this case there are suitable, in particular, chromatography (e.g. ion-exchange, Sephadex, affinity or adsorption chromatography), filtration, (e.g. ultrafiltration), electrophoresis (e.g. block, disc or carrier-free electrophoresis), isoelectric focusing and selective precipitation.

The deproteinization process provided by the present invention is especially suitable for the rapid separation of proteins in a mixture of glycoproteins. Under suitable conditions, for example, CEA (carcinoembryonic antigen: glycoprotein, molecular weight about 200,000, carbohydrate fraction about 50%) can be isolated in this manner from tumours, from liver metastases of a primary colon carcinoma or from plasma, serum and other body fluids of cancer patients. The deproteinized fluid remaining behind can be processed in any manner, for example:

For preparative purposes, the CEA extract is purified by means of further purification steps (e.g. chromatography).

For the quantitative determination of the CEA content in blood sample or in other body fluids of cancer patients, the analysis can be carried out in a suitable manner using a sensitive method such as, for example, a conventional immunological or enzyme-immunological method subsequent to the described precipitation method.

The process provided by the present invention can also be used for analytical purposes; for example, in connection with the immunological determination of immunologically-active substances such as peptides, glycoproteins, steroids, lipoids, nucleic acids, enzymes, hormones, vitamins, polysaccharides and alkaloids. In this case, the deproteinized fluid can be determined using a sensitive method such as, for example, one of the radioimmunological methods described in Clinical Chemistry, Vol 19, No. 2 (1973), 146–186, or an enzyme-immunological method described in Clinical Chemistry, Vol. 22, No. 8 (1976), 1243–1255.

Other known analytical methods such as immunofluorescence, luminescense, turbidimetry, nephelometry and kinetic-immunological methods can also be used.

The following Examples are meant to illustrate the present invention and not to restrict the invention in scope or spirit.

EXAMPLE 1

Preparation of the deproteinizing agent:

(a) 10 g of ethylene-maleic acid anhydride copolymer (EMA-21) from Monsanto Chemical Company, St. Louis Missouri, U.S.A. in the anhydride form, are dissolved in 400 ml of acetone, resulting in an EMA-21 solution. A second solution comprising 1.33 ml of ethylenediamine in 400 ml of acetone is added dropwise with stirring over a period of about 5 hours to the EMA-21 solution. After completion of the reaction, 800 ml of water are added and the acetone is removed from the reaction mixture under a vacuum in a rotary evaporator. Thereafter, the volume is made up to 1 liter with water and 5 drops of concentrated hydrochloric acid are added. After standing for 2 hours the resulting mixture is washed with water until the supernatant is almost clear, and then washed again thoroughly with acetone. The product is dried at room temperature.

(b) 540 μl of ethylenediamine are dissolved in 300 ml of water. To the resulting solution are added 5 g of Gantrez 169 from GAF Corp., Chemical Division, New York 10020, U.S.A. The resulting solution is boiled under reflux for about 15 minutes, left to stand at room temperature for 24 hours and then centrifuged. The residue is washed thoroughly with water.

(c) For the deproteinization of solutions, a fine suspension is prepared in water or in buffer by finely distributing the residue in a solvent with a tissue homogenizer (Potter type). The resulting suspension constitutes a deproteinizing agent for deproteinization.

EXAMPLE 2

Purification of CEA

A 10% (g/v) suspension of a deproteinizing agent obtained in accordance with Example 1 is prepared in twice-distilled water and finely distributed in the solvent using a tissue homogenizer (Potter type).

For the preparation of the tumour extract, 500 g of human liver metastases (autopsy material) are cut into small pieces and added to 1 liter of twice-distilled water. (All procedures are carried out at +4° C. in a cold room unless specified otherwise). A fine homogenizate is prepared in a homogenizer (Waring Blender type). After centrifugation, the protein content in the supernatant is determined using the biuret reaction. For the protein precipitation, the suspension of the deproteinizing agent is added to the supernatant (tumour tissue extract). The parts by weight of the dry weight of the suspension and of the protein content of the extract are balanced in a weight ratio of 1:1 to one another. The mixture is stirred for 15 minutes and subsequently centrifuged at 2200×g for 20 minutes. The supernatant is concentrated to 70-80 ml in a rotary evaporator at about 40° C. in vacuo. The resulting concentrate is again centrifuged after standing for 20 hours at 4° C. in order to remove later precipitations.

The clear concentrate is then chromatographed over Sephadex G 200 (5×100 cm column) and fractions of 2 ml are collected. The protein content and the CEA activity in the fractions are determined. A pool of the fractions having high CEA content is prepared. This pool is concentrated to about 10 ml in a rotary evaporator under a vacuum at about 40° C. After dialysis against twice-distilled water for 24 hours at +4° C., the purified CEA solution obtained is lyophilized.

EXAMPLE 3

Precipitation of proteins in human serum 5 g of the dry substance of the deproteinizing agent obtained in accordance with Example 1 are added to about 70 ml of twice-distilled water. A suspension of the deproteinizing agent is prepared using a tissue homogenizer (Potter type) and thereupon the suspension is made up to 100 ml with water. This concentrated suspension is diluted five times with an ammonium acetate buffer (0.01 N, pH 6.8).

For the precipitation of the serum proteins, 0.100 ml of human serum is added to 0.900 ml of the foregoing suspension. The resulting mixture is mixed briefly with a vortex stirrer and, after 5 minutes, centrifuged at 3000 revolutions per minute for 15-20 minutes using a laboratory centrifuge.

Subsequently, the CEA content is determined directly in the supernatant solution without laborious further treatment (e.g. dialysis) using a suitable method such as one of the well-known radioimmunological processes of the art.

EXAMPLE 4

Whole blood samples or plasma samples are deproteinized following the method described in Example 3 and using the deproteinizing agent obtained in accordance with Example 1.

Clinical tests can be carried out by conventional methods on the deproteinized serum, plasma or whole blood sample. In particular, uric acid, glucose, creatinine and urea can be determined in a conventional manner after carrying out the deproteinization in accordance with the invention. Haemolytic or icteric sera can also be deproteinized according to the process of the present invention following the method described in Example 3 and using the deproteinizing agent obtained in accordance with Example 1.

We claim:

1. A process for deproteinizing tumor extracts, comprising:
   (a) adding to the tumor extracts a deproteinizing agent comprising a water-insoluble crosslinked polycarbonic acid obtained by crosslinking the polymer of the formula

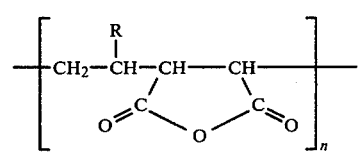

wherein R represents hydrogen or lower alkoxy and n represents a whole number of 100–10,000; with a diamine and hydrolyzing unreacted anhydride groups and
   (b) removing the resulting water-insoluble phase from the tumor extracts.

2. A process according to claim 1 wherein R represents hydrogen and n represents 120–250.

3. A process according to claim 1 wherein R represents methoxy and n represents 3,000–7500.

4. A process according to claim 1 wherein the diamine is ethylenediamine.

5. A process according to claim 1 wherein the diamine is hexamethylenediamine.

6. A process according to claim 1 wherein the tumor extracts contain glycoproteins.

7. A process according to claim 1 wherein the tumor extracts contain polysaccharides.

8. A process according to claim 1 wherein the water-insoluble phase is removed by centrifugation.

* * * * *